United States Patent [19]

Saunders

[11] Patent Number: 4,896,343
[45] Date of Patent: Jan. 23, 1990

[54] RADIATION APPARATUS WITH DISTANCE MAPPER FOR DOSE CONTROL

[76] Inventor: Allan M. Saunders, 2285 Bunker Hill Dr., San Mateo, Calif. 94402

[21] Appl. No.: 189,143

[22] Filed: May 2, 1988

[51] Int. Cl.$^4$ ............................................... H05G 1/10
[52] U.S. Cl. ..................................... 378/95; 378/108; 356/1
[58] Field of Search ......................... 378/108, 165–166, 378/204, 207, 210, 95, 151; 356/1

[56] References Cited

U.S. PATENT DOCUMENTS

| 3,502,878 | 3/1970 | Stewart et al. | 378/151 |
|---|---|---|---|
| 3,516,743 | 6/1970 | McKown et al. | 356/4 |
| 3,530,468 | 9/1970 | Hannan | 343/15 |
| 3,554,646 | 1/1971 | Carlson | 356/1 |
| 3,565,528 | 2/1971 | Witte | 356/5 |
| 3,610,754 | 10/1971 | Pirlet | 356/1 |
| 3,861,807 | 1/1975 | Lescrenier | 378/65 |
| 3,954,335 | 5/1976 | Bodlaj | 356/4 |
| 4,059,758 | 11/1977 | Wilwerding | 356/1 |
| 4,137,460 | 1/1979 | Fitzsimmons et al. | 378/117 |
| 4,212,534 | 7/1980 | Bodlaj | 356/1 |
| 4,218,138 | 8/1980 | Robertsson | 356/152 |
| 4,403,337 | 9/1983 | Kleinman | 378/95 |
| 4,597,094 | 6/1986 | Kleinman | 378/95 |
| 4,639,140 | 1/1987 | Lerat | 356/376 |
| 4,647,209 | 3/1987 | Neukomm et al. | 356/1 |

Primary Examiner—Craig E. Church
Assistant Examiner—John C. Freeman
Attorney, Agent, or Firm—Thomas Schneck

[57] ABSTRACT

An irradiation apparatus including an x-ray or gamma-ray source, an optical distance and surface profile measuring device, and means for adjusting the dose of radiation delivered to a target surface by the source based on a precise measured distance from the source to the target surface. The measuring device has a laser or other beam source and photodetector in known fixed relationship to the radiation source, and a pair of mirrors which are turnable to direct the laser beam from the laser to a sequence of selected spots on the target surface and then to the photodetector. Knowing the geometry of the system, the distance from the radiation source to the sequence of spots on the target surface can be computed. In one embodiment the two mirrors define a baseline of a triangle, with the laser and photodetector lying proximate to the baseline. One mirror rotates at a known speed and sensors determine the orientation of the mirror when that mirror directs light reflected from the target onto the photodetector. The orientation angles of the mirror, together with the width of the baseline, determine the altitude of the triangle formed by the mirrors and the target surface. The altitude combined with the known distance of the radiation source to the baseline determine distances for a profile of the surface. A plurality of profiles form a three-dimensional topographic surface map.

15 Claims, 2 Drawing Sheets

RADIATION APPARATUS WITH DISTANCE MAPPER FOR DOSE CONTROL

DESCRIPTION

TECHNICAL FIELD

The present invention relates to apparatus for delivering a specific therapeutic dose of x-rays or the like to a target, using optical distance and surface profile measuring equipment.

BACKGROUND ART

In U.S. Pat. No. 4,403,337, Kleinman discloses a medical x-ray machine using acoustic pulse-echo ranging in order to automatically determine and set the amount of current and voltage supplied to an x-ray source, as well as the exposure time, based on the thickness of the patient part to be imaged. The ranging system includes a sonic transducer at a known distance from a receptor, and a circuit which determines the travel time of a sonic signal from the transducer to the patient and back to the receptor. The thickness of the patient part can be determined from the actual travel time compared to the time when no patient is present.

In U.S. Pat. No. 4,212,534, Bodlaj describes a device for contact-free measuring of the distance of an object surface from a reference plane having a laser light source producing a beam of light, a light deflector causing the beam to repeatedly scan over the surface of an object and a photodetector. The device measures the interval of time for travel of the beam for at least two specific directions of the beam, and between one of the two directions and a direction at which the detector responds, and uses these intervals to determine the distance.

X-ray or gamma ray apparatus generally produce a divergent beam whose intensity decreases with distance according to an inverse square relationship. Accordingly, in order to deliver a precise dose to a medical patient in order to form a good image on a film plate or to irradiate a tumor without unduly exposing the patient to excess radiation, the precise distance of the patient from the x-ray source must be found. Other factors related to distance which are used in making a precise dose calculation include the thickness of a body part to receive x-rays and the skin surface profile of the area to be irradiated. Previous measurement techniques such as using rulers and calipers to determine distance and thickness, and acoustic measurements, are usually adequate for forming viewable x-ray images on a photographic plate but are not sufficiently accurate for delivering a precise dose to a tumor in a localized area.

It is an object of the present invention to produce an x-ray or gamma ray apparatus with a distance measuring system capable of more accurately determining the precise radiation dose to be delivered to a target area surface of a patient.

DISCLOSURE OF THE INVENTION

The above objects have been met with an optical target profiling system used prior to the use of a radiation treatment process. The target profiler maps a surface, such as a portion of a patient's body so that radiation dose to a portion of the body can be carefully controlled. By creating a topographic map or a series of profiles, the contours of a surface region of the body may be taken into account. Now, three dimensional information is available regarding the target, rather than the one dimensional information of the prior art. The entire apparatus includes an x-ray or isotopic source for producing an x-ray or gamma ray beam directed so as to deliver a dose of radiation to an area of a target surface, an optical distance and surface profile measuring device, and means responsive to the measured distance from the x-ray or isotopic source to the target surface for adjusting the dose of radiation produced by the source. The laser distance and profile measuring device includes a laser or other beam source emitting a light beam and also includes a photodetector, both in known spatial relationship to the source. Mirrors or other means for directing the light beam to a sequence of spots on the target area and for directing light scattered and reflected from the target to the photodetector are provided. Knowing the geometry of the system, including for example, the angles of the directing mirrors, one can compute the distance from the x-ray source to each spot on the target area and produce a surface profile map. The profile map alone is very valuable where distance is measured by another technique or approximated, but profile plus distance is even more valuable. One embodiment rotates a mirror at a known speed. Sensors determine when the mirror is in a known orientation, while the photodetector senses when the light from the target is properly directed to the detector. The time lag between the two times is used to determine the angle of the mirror for computation purposes. Once the surface profile is known, the radiation beam may be attenuated to deliver a desired dose to the target body.

BEST MODE FOR CARRYING OUT THE INVENTION

Figure 1:
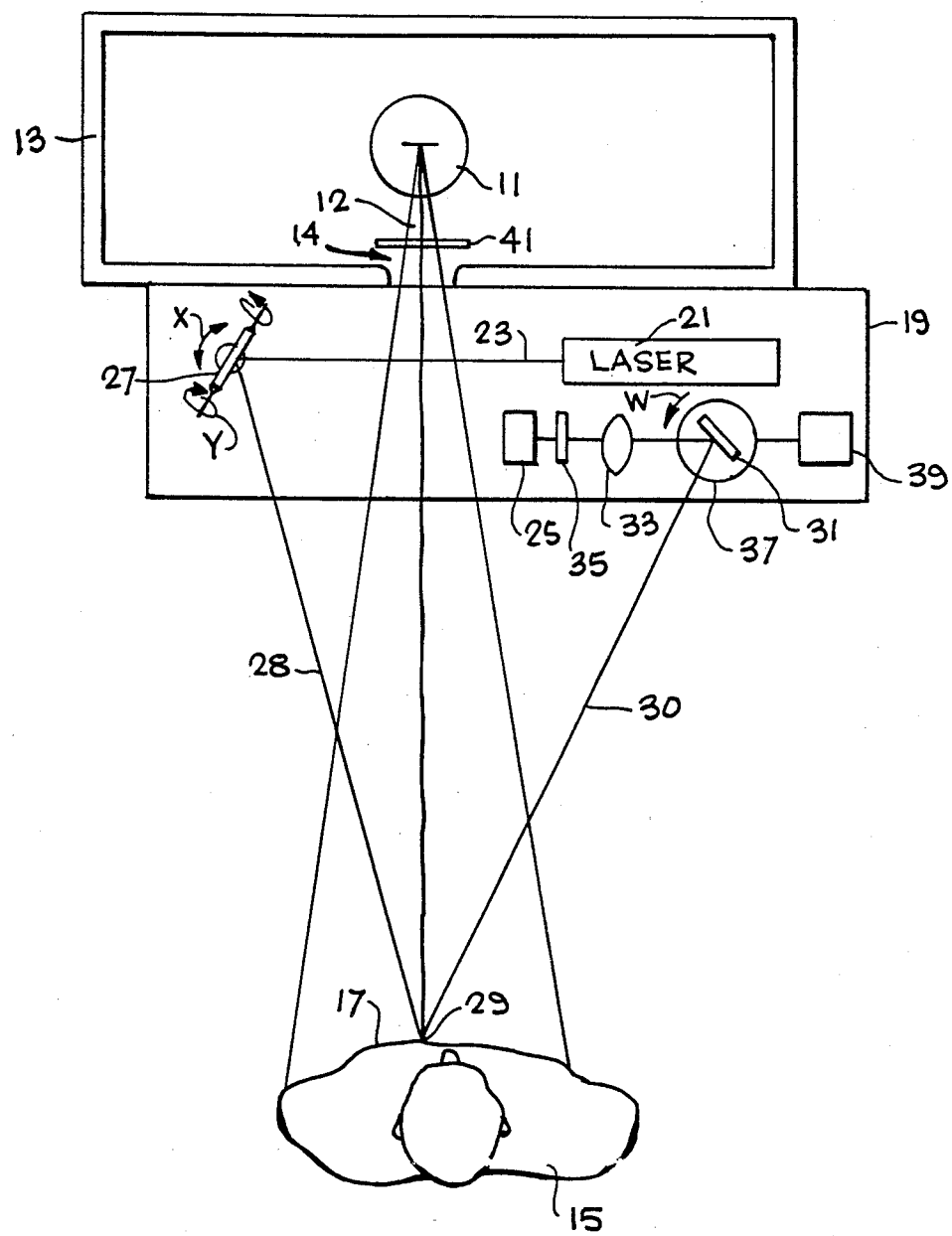
FIG. 1 is a top plan view of an x-ray apparatus of the present invention.

With reference to FIG. 1, an x-ray or other ionizing radiation source 11 contained in a shielding box 13 produces a beam 12 directed through an aperture 14 in shielding box 13 to a target 15. Beam 12 is a divergent beam and delivers a dose of radiation to a surface area 17 of target 15 according to the inverse square of the distance from the source to the surface 17. Radiation source 11 is typically an electrically powered x-ray tube. Alternatively, source 11 may be a radioactive isotope producing gamma rays. The dose of x-rays delivered to target 15 by an x-ray tube can be adjusted by adjusting the voltage or current or both which energizes the x-ray tube. The dose may also be adjusted by varying the attenuation provided by x-ray or gamma ray attenuating filters 41 in the path of beam 12. Typically target 15 is a patient undergoing medical diagnosis or treatment. However, the x-ray apparatus may also be used for other types of targets.

In order to administer a precise dose of x-rays to a target area, it is necessary to measure the distance from the x-ray source 11 to the target area surface 17. Since a target with many surface features has varying distances to the x-ray source depending on the point being used for measurement, it is preferable that a topographic may be developed of the area of the target surface to receive x-rays. Attenuator 41 need not be a flat plate, and can be a custom built part. It is known in the art that one can make an attenuator with a controlled thickness or attenuation profile, such that the target gets a uniform dose or to adjust the dose locally as required in order to compensate for tissue behavior, using profile information obtained from distance measurements. The present invention includes an optical distance and surface profile mapping device 19, which computes the required distances for various points on the target surface.

The device 19 includes a laser or other beam source 21 emitting a light beam 23 and a photodetector 25. Laser 21 and photodetector 25 are in a known spatial relationship with respect to x-ray source 11. A first mirror 27 in a path of light beams 23 directs light beam 23 from laser 21 towards a sequence of spots 29 on target surface 17. First mirror 27 is turnable about at least one axis, as indicated by arrows X in order to place spot 29 of laser light 23 where required on target surface 17. Preferably, first mirror 27 may be turned about two axes, as indicated by arrows X and arrow Y. By swinging first mirror 27 in two directions, an area can be scanned and the contour of the area can be generated. Alternatively, mirror 27 may be replaced by a pair of mirrors turnable about respective orthogonal axes. Laser light 23 after having been redirected by first mirror 27 onto path 28 to spots 29 is scattered by target surface 17, and the scattered light along the path 30 is directed by a second mirror 31 to photodetector 25. A lens 33 focuses the light from mirror 31 onto photodetector 25, and a color filter 35 blocks unwanted light of colors other than that of laser 21.

A motor 37 rotates second mirror 31 at a known and preferably constant speed. As mirror 31 rotates, a sensor 39 detects when mirror 31 reaches a predetermined orientation. Sensor 39 then generates a start signal. Then as mirror 31 continues to rotate, it reaches an orientation where light scattered from point 29 on target surface 17 reaches photodetector 25. Photodetector 25 generates a signal on receiving light from spot 29. The orientation of mirror 31 when detection by photodetector 15 occurs is determined by the time lag between the start signal from sensor 39 and the detection signal from photodetector 25, together with the known speed of rotation of mirror 31. Photodetector 25 is preferably a differential sensing split area detector. This allows sensing of the exact moment at which the scanning mirror 31 is positioned to reflect the laser spot from the target surface 17 into the midpoint of photodetector 25. Midpoint sensing is preferred because temperature, laser power, ambient light, and other parameters affect both halves of the detector equally, therefore cause no differential signal at the midpoint. A phase-locked loop may be used to synchronize the speed of the time base used in determining the angular orientation of mirror 31 to match the motor speed of motor 37. This allows precise prediction of the angular position of the scanning mirror 31 without the use of an expensive precision motor shaft position encoder. Precision motor shaft position encoders may also be used. The angular orientation of first mirror 27 is known from a shaft angle encoder, galvanometer or other means.

Figure 2:
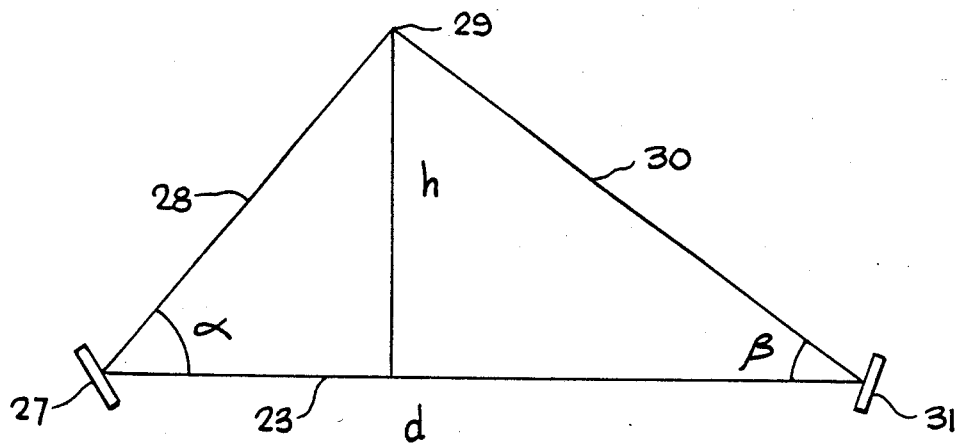
FIG. 2 is a schematic diagram illustrating the triangulation geometry for the apparatus in FIG. 1.

With reference to FIG. 2, the distance from the x-ray source to each of the sequence of spots on target surface 17 may be computed from the known geometry of the apparatus, such as by triangulation using the angles of first and second mirrors 27 and 31. For example, the path of laser beam 23 from laser 21 to first mirror 27 defines a baseline represented in FIG. 2 by the base 23 of the triangle. The orientation of first mirror 27 is characterized by an angle $\alpha$ between the baseline and a path 28 between first mirror 27 and the desired spot 29 on the target surface. Likewise the orientation of second mirror 31 is characterized by an angle $\beta$ between the baseline and a path 30 between the desired spot 29 on the target surface and second mirror 31. Mirror 31 and the photodetector are located proximate to the baseline 23 to minimize any errors in the calculation of the desired distances. Knowing the distance d between first and second mirrors 27 and 31 along baseline 23 and knowing the characteristic angles $\alpha$ and $\beta$ mirrors 27 and 31 the height h, which represents the distance between the baseline 23 and the desired spot 29 on the target surface, may be found according to the formula:

$$\frac{h}{d} = [\cot \alpha + \cot \beta]^{-1}$$

since the laser source photodetector and mirrors of the distance measuring apparatus 19 are in a known relationship to the x-ray source, the distance x between the x-ray source and a baseline 23 is known. Accordingly, the distance D between the x-ray source and each of the sequence of desired spots 29 on the target surface is $D = x + d[\cot \alpha + \cot \beta]^-$. This process may be repeated for each of the sequence of points on the target surface.

The triangulation example just given is not the only way to compute the desired distance measurements. The geometrical relationship between the laser or other beam source, the scanning mirrors, target and detector can be quite complex. However, once the geometry is known the distance can be computed from a derived formula based on that geometry using measurements of predetermined parameters. Since the geometry is fixed for a particular apparatus, the geometric formula for computing the desired distance need be derived only once.

A surface profile map may be formed from the computed distances for the sequence of points on the target surface. If the first mirror 27 is turnable about one axis the locus of points represents a line on the target surface whereas areawise coverage of the target surface is provided when first mirror 27 is scannable about two axes, or when multiple scanning mirrors are used.

Figure 3:
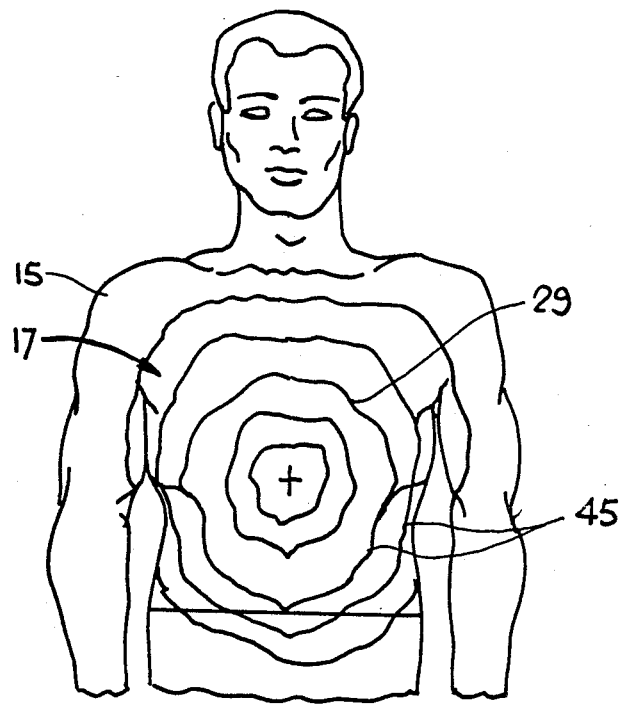
FIG. 3 is a profile map corresponding to a front plan view of a target surface to receive x-rays from the apparatus in FIG. 1.

With reference to FIG. 3, a surface profile map represented by a series of equidistant curves 45 is seen overlaid over a front view of a target 15, here a patient undergoing medical treatment. The target surface is in this instance the front torso of patient 15. A three-dimensional map of the target is made with a series of scans across the target. Each curve 45 represents a plurality of points 29 calculated to have the same distance from the x-ray source. This three-dimensional map combined with the distances are used to adjust the x-ray dose which the patient 15 receives. The patient 15 may for example be receiving x-rays for the treatment of a tumor located in a specific organ of his or her body, and the treatment may require a specified minimum dose of x-rays directed to that organ while at the same time the rest of the body 15 should not receive an excess amount of x-rays. Knowing the amount of tissue between the skin surface and the target organ and knowing the attenuation factors for that intervening tissue, the amount of x-rays can be fine tuned so that the target organ receives the precise dose required. As already noted above, the attenuator 41 in FIG. 1 need not be a flat plate but can have a controlled three-dimensional profile custom made for the particular patient. The surface profile map is used to make this custom attenuator. Since some patients may require several doses over a period of weeks or months, the particular attenuator can be saved and brought out again for the next treatment dose.

The x-ray apparatus of the present invention allows precise dosage calculations to be made based upon an optical beam base distance and surface profile mapping device which is estimated to be accurate to within one millimeter within the area to be covered by the x-ray beam.

I claim:

1. Apparatus for delivering a radiation dose comprising, radiation source means for producing a beam of ionizing gamma ray or x-ray radiation directed so as to deliver a dose of said radiation to an area of a target surface, a light source emitting a light beam in a direction transverse to the direction of the ionizing radiation beam, a photodetector, positioned to receive light scattered from the target surface, means for scanning the light beam over the area of the target surface, means for forming a three-dimensional surface profile map of said area of the target surface without movement of the radiation source means or of the light source, and means responsive to said surface profile map for adjusting said dose of radiation from said radiation source over the area of the target surface, so that the radiation source means and the light source may be operated simultaneously.

2. Apparatus for delivering a specific radiation dose to a target comprising, radiation source means for producing a beam of ionizing gamma ray or x-ray radiation directed to as to deliver a dose of such radiation to an area of a target surface, a light source emitting a light beam in a direction transverse to the direction of the ionizing radiation beam, a photodetector, positioned to receive scattered light from the target surface, means for directing said light beam from said light source to a sequence of desired spots in said area on said target surface and for directing light scattered and reflected from said sequence of desired spots to said photodetector without movement of the radiation source means or of the light source, means for computing the distances from said radiation source to each of said desired spots on said target surface and for constructing a three-dimensional surface profile map of said area of said target surface, and means responsive to said distances and said surface profile map for adjusting said dose of radiation from said radiation source, so that the radiation source means and the light source may be operated simultaneously.

3. Apparatus for delivering a specific radiation dose to a target, the apparatus comprising, radiation source means for producing a beam of ionizing gamma ray or x-ray radiation directed so as to deliver a dose of such radiation to a chosen area of a target surface, a light source emitting a light beam, a photodetector positioned to receive the light beam from the light source, control means for directing the light beam from the light source to a sequence of desired spots in the chosen area on the target surface and for directing light scattered and reflected from the sequence of desired spots to the photodetector, the directing means comprising, a first mirror positioned in a path of the light beam, the light source and the first mirror defining a baseline therebetween, with the first mirror being rotatable about at least one axis so as to redirect an incident light beam to any of the sequence of desired spots, the orientation of the first mirror being characterized by an angle between the baseline and a path between the first mirror and a desired spot on the target surface, and a second mirror positioned to receive light scattered and reflected from a desired spot on the target surface, the second mirror being orientable so as to direct at least a portion of the scattered and reflected light toward the photodetector, the orientation of the second mirror being characterized by an angle between the baseline and a path between a desired spot on the target surface and the second mirror, computer means for computing the distances from said radiation source to each of the desired spots on said target surface and for constructing a three-dimensional surface profile map of said area of the target surface, and adjustment means responsive to said distances and said surface profile map for adjusting the dose of radiation from the radiation source.

4. The apparatus of claim 3 wherein said means for geometrically computing comprises a processor for triangulating from a known distance x between said radiation source and said baseline, a known distance d between said first and second mirrors and said angles $\alpha$ and $\beta$, a distance D between said radiation source and each of said sequence of desired spots on said target surface, where $$D = x + d[Cot\alpha + Cot\beta]^{-1}.$$

5. The apparatus of claim 3 further comprising means for rotating said second mirror at a known speed, and means for determining said angle $\beta$.

6. The apparatus of claim 5 wherein determining said angle $\beta$ comprises, means for sensing times when said second mirror is in a predetermined orientation, said sensing means generating a start signal at said times, means for determining a time lag between said start signal and a light detection signal from said photodetector, and means for calculating from said time lag and said speed of said second mirror the angle $\beta$.

7. An x-ray apparatus with laser distance mapper comprising, a radiation source for producing a beam of game ray or x-ray radiation directed so as to deliver a dose of said radiation to an area of a target surface, a laser emitting a light beam, a first mirror in a path of said light beam, the laser and said first mirror defining a baseline therebetween, said first mirror being turnable about at least one axis and oriented so as to redirect said light beam toward a sequence of spots on said target surface, the orientation of said first mirror characterized by an angle $\alpha$ between said baseline and a path of said redirected light from said first mirror to said desired spot, said light beam being scattered and reflected by said target surface, a second mirror disposed proximate to said baseline a known distance d away from said first mirror, means for orienting said second mirror to direct said reflected and scattered light parallel to said baseline, a photodetector disposed proximate to said baseline between said first and second mirrors, said photodetector receiving said scattered and reflected light from said target surface via said second mirror when said second mirror is oriented to reflect said light an angle $\beta$, said angle $\beta$ defined between a path of said scattered and reflected light from one said desired spot on said target surface to said second mirror and said baseline, said photodetector generating a light detection signal upon receiving said light, means for determining said angle $\beta$, means for calculating a distance D from said radiation source to each said spot on said target surface, where $D = x + d[\cot\alpha + \cot\beta]^{-1}$, x being the distance from said radiation source to said baseline, means responsive to said calculated distance D for attenuating said radiation beam.

8. The apparatus of claim 7 wherein said first mirror is turnable about two orthogonal axes.

9. The apparatus of claim 7 further defined by means for turning said first mirror in a scanning pattern so as to scan said light beam over said area of said target surface, and means for constructing a surface profile map of said area of said target surface from a set of distances D for a set of spots scanned by said light beam.

10. The apparatus of claim 9 wherein said attenuating means comprise attenuating filters having a controlled profile based on said surface profile map.

11. The apparatus of claim 7 wherein said means for orientating said second mirror comprises means for rotating said second mirror at a known speed.

12. The apparatus of claim 11 wherein said means for determining said angle $\beta$ comprises, a sensor generating a start signal at times when said second mirror is in a predetermined orientation, means for determining a time difference between said start signal and said light detection signal, means for calculating said angle $\beta$ from said time difference and said speed of said second mirror.

13. The apparatus of claim 7 wherein said photodetector comprises a split area detector.

14. The apparatus of claim 7 wherein said radiation source comprises an x-ray tube producing x-rays.

15. The apparatus of claim 7 wherein said radiation source comprises a radioactive isotope producing $\gamma$-rays.

* * * * *

UNITED STATES PATENT AND TRADEMARK OFFICE
CERTIFICATE OF CORRECTION

PATENT NO. : 4,896,343
DATED : January 23, 1990
INVENTOR(S) : Allan M. Saunders

It is certified that error appears in the above-identified patent and that said Letters Patent is hereby corrected as shown below:

Column 2, line 68, "may" should read - - map - -.

Column 3, line 43, "15" should read - - 25 - -.

Column 4, line 29, "$[\cot \alpha + \cot \beta]^-.$" should read - - $[\cot \alpha + \cot \beta]^{-1}.$ - -.

Claim 2, column 5, line 42, "directed to as to" should read - - directed so as to - -.

Claim 7, column 6, line 65, "of game ray" should read - - of ionizing gamma ray - -.

Signed and Sealed this

Twelfth Day of March, 1991

*Attest:*

HARRY F. MANBECK, JR.

*Attesting Officer*   *Commissioner of Patents and Trademarks*